US011617861B2

(12) United States Patent
Pai et al.

(10) Patent No.: US 11,617,861 B2
(45) Date of Patent: *Apr. 4, 2023

(54) TRIPLE COIL CATHETER SUPPORT

(71) Applicant: St. Jude Medical, Cardiology Division, Inc., St. Paul, MN (US)

(72) Inventors: Sameer D. Pai, Plymouth, MN (US); Zachary L. Helgeson, Richfield, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 187 days.

This patent is subject to a terminal disclaimer.

(21) Appl. No.: 17/101,944

(22) Filed: Nov. 23, 2020

(65) Prior Publication Data

US 2021/0069474 A1    Mar. 11, 2021

Related U.S. Application Data

(60) Continuation of application No. 16/403,284, filed on May 3, 2019, now Pat. No. 10,869,992, which is a (Continued)

(51) Int. Cl.
*A61M 25/00* (2006.01)
*A61M 25/01* (2006.01)
(Continued)

(52) U.S. Cl.
CPC ..... *A61M 25/0147* (2013.01); *A61B 5/02158* (2013.01); *A61B 5/02444* (2013.01); *A61B 5/287* (2021.01); *A61B 5/6852* (2013.01); *A61B 18/1492* (2013.01); *A61B 2018/00351* (2013.01); *A61B 2018/00577* (2013.01); *A61B 2018/00839* (2013.01); *A61M 2025/0046* (2013.01)

(58) Field of Classification Search
CPC .......................... A61M 25/0147; A61B 5/287
USPC ............................................... 604/95; 606/41
See application file for complete search history.

(56) References Cited

U.S. PATENT DOCUMENTS 5,224,939 A    7/1993    Holman et al.
5,380,301 A    1/1995    Prichard et al.
(Continued)

FOREIGN PATENT DOCUMENTS

CN    101927053 B    1/2015
CN    103157168 B    4/2015
(Continued)

*Primary Examiner* — Nicole F Lavert
(74) *Attorney, Agent, or Firm* — Kilpatrick Townsend & Stockton LLP

(57) ABSTRACT

A catheter with three distinct compression resistance coils, including a body coil and two pull wire coils, is disclosed. The triple coil system can provide maximal resistance to compression of the catheter's proximal shaft, as well as maximization of the curve angle that the catheter tip can achieve. Additionally, the tri-coil catheter can allow for a lower initial compression load and a more flexible proximal shaft. A gap between the outer diameter of the pull wire and the inner diameter of the pull wire compression coil that is equal to about 10-30% of inner diameter of the pull wire compression coil can provide optimal catheter performance.

20 Claims, 5 Drawing Sheets

Related U.S. Application Data division of application No. 15/832,558, filed on Dec. 5, 2017, now Pat. No. 10,322,261, which is a division of application No. 14/729,822, filed on Jun. 3, 2015, now Pat. No. 9,844,645.

(60) Provisional application No. 62/013,447, filed on Jun. 17, 2014.

(51) Int. Cl.
| | |
|---|---|
| *A61B 18/14* | (2006.01) |
| *A61B 5/00* | (2006.01) |
| *A61B 5/0215* | (2006.01) |
| *A61B 5/024* | (2006.01) |
| *A61B 5/287* | (2021.01) |
| *A61B 18/00* | (2006.01) |

(56) References Cited

U.S. PATENT DOCUMENTS

| | | | |
|---|---|---|---|
| 5,400,783 | A | 3/1995 | Pomeranz et al. |
| 5,456,254 | A | 10/1995 | Pietroski et al. |
| 5,626,136 | A | 5/1997 | Webster, Jr. |
| 5,715,817 | A | 2/1998 | Stevens-Wright et al. |
| 5,715,832 | A | 2/1998 | Koblish et al. |
| 5,827,278 | A | 10/1998 | Webster, Jr. |
| 5,876,373 | A | 3/1999 | Giba et al. |
| 6,074,379 | A | 6/2000 | Prichard |
| 6,198,974 | B1 | 3/2001 | Webster, Jr. |
| 6,273,404 | B1 | 8/2001 | Holman et al. |
| 6,491,681 | B1 | 12/2002 | Kunis et al. |
| 6,554,794 | B1 | 4/2003 | Mueller et al. |
| 7,004,937 | B2 | 2/2006 | Lentz et al. |
| 7,214,220 | B2 | 5/2007 | McGlinch et al. |
| 7,217,256 | B2 | 5/2007 | Di Palma |
| 7,608,063 | B2 | 10/2009 | Le et al. |
| 7,625,365 | B2 | 12/2009 | McGlinch et al. |
| 7,666,204 | B2 | 2/2010 | Thornton et al. |
| 7,959,601 | B2 | 6/2011 | McDaniel et al. |
| 7,985,215 | B2 | 7/2011 | Guo et al. |
| 8,103,327 | B2 | 1/2012 | Harlev et al. |
| 8,137,321 | B2 | 3/2012 | Argentine |
| 8,221,390 | B2 | 7/2012 | Pal et al. |
| 8,273,016 | B2 | 9/2012 | O'sullivan |
| 8,376,990 | B2 | 2/2013 | Ponzi et al. |
| 8,447,377 | B2 | 5/2013 | Harlev et al. |
| 8,608,703 | B2 | 12/2013 | Riles et al. |
| 8,649,880 | B1 | 2/2014 | Parker, Jr. |
| 8,700,120 | B2 | 4/2014 | Koblish |
| 8,706,193 | B2 | 4/2014 | Govari et al. |
| 8,755,861 | B2 | 6/2014 | Harlev et al. |
| 8,777,929 | B2 | 7/2014 | Schneider et al. |
| 8,792,962 | B2 | 7/2014 | Esguerra et al. |
| 8,814,824 | B2 | 8/2014 | Kauphusman et al. |
| 8,814,825 | B2 | 8/2014 | Tegg et al. |
| 8,882,705 | B2 | 11/2014 | McDaniel et al. |
| 8,894,610 | B2 | 11/2014 | Macnamara et al. |
| 8,996,091 | B2 | 3/2015 | de la Rama et al. |
| 9,017,308 | B2 | 4/2015 | Klisch et al. |
| 9,033,917 | B2 | 5/2015 | Magana et al. |
| 9,050,010 | B2 | 6/2015 | Bui et al. |
| 9,101,733 | B2 | 8/2015 | McDaniel |
| 9,204,929 | B2 | 12/2015 | Solis |
| 9,216,056 | B2 | 12/2015 | Datta et al. |
| 9,247,990 | B2 | 2/2016 | Kauphusman et al. |
| 9,326,815 | B2 | 5/2016 | Watson |
| 9,339,631 | B2 | 5/2016 | Graham et al. |
| 9,433,751 | B2 | 9/2016 | Ponzi et al. |
| 9,433,752 | B2 | 9/2016 | Jimenez et al. |
| 9,468,495 | B2 | 10/2016 | Kunis et al. |
| 9,486,280 | B2 | 11/2016 | Koblish et al. |
| 9,486,282 | B2 | 11/2016 | Solis |
| 9,539,413 | B2 | 1/2017 | Ogle |
| 9,649,158 | B2 | 5/2017 | Datta et al. |
| 9,687,166 | B2 | 6/2017 | Subramaniam et al. |
| 9,694,159 | B2 | 7/2017 | Schneider et al. |
| 9,694,161 | B2 | 7/2017 | Selkee |
| 9,788,895 | B2 | 10/2017 | Solis |
| 9,919,132 | B2 | 3/2018 | Tegg et al. |
| 9,986,949 | B2 | 6/2018 | Govari et al. |
| 10,004,877 | B2 | 6/2018 | Tegg |
| 10,034,637 | B2 | 7/2018 | Harlev et al. |
| 10,052,457 | B2 | 8/2018 | Nguyen et al. |
| 10,065,019 | B2 | 9/2018 | Hamuro et al. |
| 10,099,036 | B2 | 10/2018 | Heideman et al. |
| 10,118,022 | B2 | 11/2018 | Helgeson et al. |
| 10,143,394 | B2 | 12/2018 | Solis |
| 10,384,036 | B2 | 8/2019 | Romoscanu |
| 10,398,500 | B2 | 9/2019 | Huszar et al. |
| 10,556,091 | B2 | 2/2020 | Truhler et al. |
| 10,575,745 | B2 | 3/2020 | Solis |
| 10,646,692 | B2 | 5/2020 | Tegg et al. |
| 10,653,423 | B2 | 5/2020 | Starnes |
| 10,835,712 | B2 | 11/2020 | Wada |
| 10,842,990 | B2 | 11/2020 | de la Rama et al. |
| 10,857,349 | B2 | 12/2020 | de la Rama et al. |
| 10,898,685 | B2 | 1/2021 | Tegg |
| 10,967,150 | B2 | 4/2021 | Helgeson et al. |
| 11,160,482 | B2 | 11/2021 | Solis |
| 11,172,858 | B2 | 11/2021 | Olson et al. |
| 2001/0018596 | A1* | 8/2001 | Selmon ............... A61M 29/02 606/198 |
| 2002/0165484 | A1 | 11/2002 | Bowe et al. |
| 2007/0270679 | A1 | 11/2007 | Nguyen et al. |
| 2014/0100639 | A1 | 4/2014 | Lee et al. |
| 2015/0119911 | A1 | 4/2015 | Mckenzie |
| 2016/0213423 | A1 | 7/2016 | Kauphusman et al. |
| 2020/0138378 | A1 | 5/2020 | de la Rama et al. |
| 2020/0253496 | A1 | 8/2020 | Deno et al. |
| 2021/0145342 | A1 | 5/2021 | Wang |
| 2021/0268234 | A1 | 9/2021 | Helgeson et al. |
| 2022/0023594 | A1 | 1/2022 | Pai |
| 2022/0054066 | A1 | 2/2022 | Solis |

FOREIGN PATENT DOCUMENTS

| | | |
|---|---|---|
| CN | 104434083 B | 4/2019 |
| CN | 104968261 B | 5/2019 |
| CN | 105592778 B | 7/2019 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2604306 B1 | 1/2014 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |
| EP | 3057488 B1 | 5/2018 |
| EP | 2848226 B1 | 7/2018 |
| EP | 3391928 A1 | 10/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3466363 A1 | 4/2019 |
| EP | 2550989 B1 | 6/2019 |
| EP | 2908723 B1 | 3/2020 |
| EP | 3738508 A1 | 11/2020 |
| EP | 3738509 A1 | 11/2020 |
| EP | 2155301 B1 | 4/2021 |
| EP | 2809254 B1 | 6/2021 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |

(56) References Cited

FOREIGN PATENT DOCUMENTS

| | | | |
|---|---|---|---|
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 2017051211 | A | 3/2017 |
| JP | 6246742 | B2 | 12/2017 |
| JP | 6434495 | B2 | 12/2018 |
| JP | 6445509 | B2 | 12/2018 |
| JP | 6466114 | B2 | 2/2019 |
| JP | 6515084 | B2 | 4/2019 |
| JP | 6980386 | B2 | 11/2021 |
| WO | 9843530 | A1 | 10/1998 |
| WO | 0168178 | A1 | 9/2001 |
| WO | 2008091197 | A1 | 7/2008 |

\* cited by examiner

TRIPLE COIL CATHETER SUPPORT

CROSS-REFERENCE TO RELATED APPLICATIONS

This application is a continuation of U.S. application Ser. No. 16/403,284, filed 3 May 2019 (the '284 application); which is a division of U.S. application Ser. No. 15/832,558, filed 5 Dec. 2017 (the '558 application), now issued as U.S. Pat. No. 10,322,261 on 18 Jun. 2019; which is a division of U.S. application Ser. No. 14/729,822, filed 3 Jun. 2015 (the '822 application), now issued as U.S. Pat. No. 9,844,645 on 19 Dec. 2017; which claims the benefit of U.S. provisional application No. 62/013,447, filed 17 Jun. 2014 (the '447 application). The '284 application, the '558 application, the '822 application, and the '447 application are all hereby incorporated by reference in their entirety as though fully set forth herein.

BACKGROUND a. Field of the Disclosure

The instant disclosure relates generally to a deflectable catheter shaft, and particularly to a catheter shaft with compression resistance coils.

b. Background Art

Electrophysiology catheters are used in a variety of diagnostic, therapeutic, mapping, and ablation procedures to diagnose and/or correct conditions such as atrial arrhythmias, including, for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, all of which can lead to a variety of symptomatic and asymptomatic ailments and even death.

Typically, a catheter is deployed and manipulated through a patient's vasculature to the intended site—for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

To facilitate the advancement of catheters through a patient's vasculature, the proximal end of the catheter can be manipulated to guide the catheter through vessels and heart chambers. The simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The distal tip can be deflected by one or more pull wires attached at the distal end of the catheter that extends proximally to a control handle, for example, that controls the application of tension on the pull wire or pull wires.

Two of the mechanical considerations for a catheter shaft are that it transmit torque and resist compression during use. With respect to transmitting torque, medical personnel normally navigate the distal end of the catheter to a desired location in part by manipulating a handle disposed at the proximal end of the catheter shaft, or by rolling the proximal portion of the catheter shaft about its longitudinal axis with their fingers. Substantial frictional forces sometimes resist transmission of torque down the length of the catheter. With respect to resisting compression during use, catheter shafts may include compression coils that may comprise a plurality of stacked coils, such that the catheter shaft may be laterally deflected or curved while resisting longitudinal compression and the concomitant problems that such longitudinal compression may cause.

The foregoing discussion is intended only to illustrate the present field and should not be taken as a disavowal of claim scope.

BRIEF SUMMARY

Embodiments of the present disclosure provide a catheter with three distinct compression resistance coils, including a body coil and two pull wire coils. The triple coil system can provide maximal resistance to compression of the catheter's proximal shaft, as well as maximization of the curve angle that the catheter tip can achieve. Additionally, the tri-coil catheter can allow for a lower initial compression load and a more flexible proximal shaft. A gap between the outer diameter of the pull wire and the inner diameter of the pull wire compression coil that is equal to about 10-30% of inner diameter of the pull wire compression coil can provide optimal catheter performance.

In accordance with an aspect of the present disclosure, a steerable catheter comprises a shaft comprising a proximal end, a distal end, and a central lumen; a distal deflectable section of the shaft, the distal deflectable section comprising a proximal end and a distal end; a body compression coil surrounded by the shaft and extending through the central lumen from the proximal end of the shaft to the proximal end of the distal deflectable section; at least one pull wire extending through the body compression coil from the proximal end of the shaft to the proximal end of the distal deflectable section; and a pull wire compression coil surrounding the pull wire within the body compression coil, the pull wire compression coil extending from the proximal end of the shaft to the proximal end of the distal deflectable section.

In accordance with another aspect of the present disclosure, a steerable catheter comprises a shaft comprising a proximal end, a distal end, and a central lumen; a distal deflectable section of the shaft, the distal deflectable section comprising a proximal end and a distal end; at least one pull wire extending through the shaft from the proximal end of the shaft to the proximal end of the distal deflectable section; and a pull wire compression coil surrounding the pull wire, the pull wire compression coil extending from the proximal end of the shaft to the proximal end of the distal deflectable section; wherein a gap between an outer diameter of the pull wire and an inner diameter of the pull wire compression coil is about 10%-30% of the inner diameter of the pull wire compression coil.

The foregoing and other aspects, features, details, utilities, and advantages of the present disclosure will be apparent from reading the following description and claims, and from reviewing the accompanying drawings.

DETAILED DESCRIPTION

Figure 1:
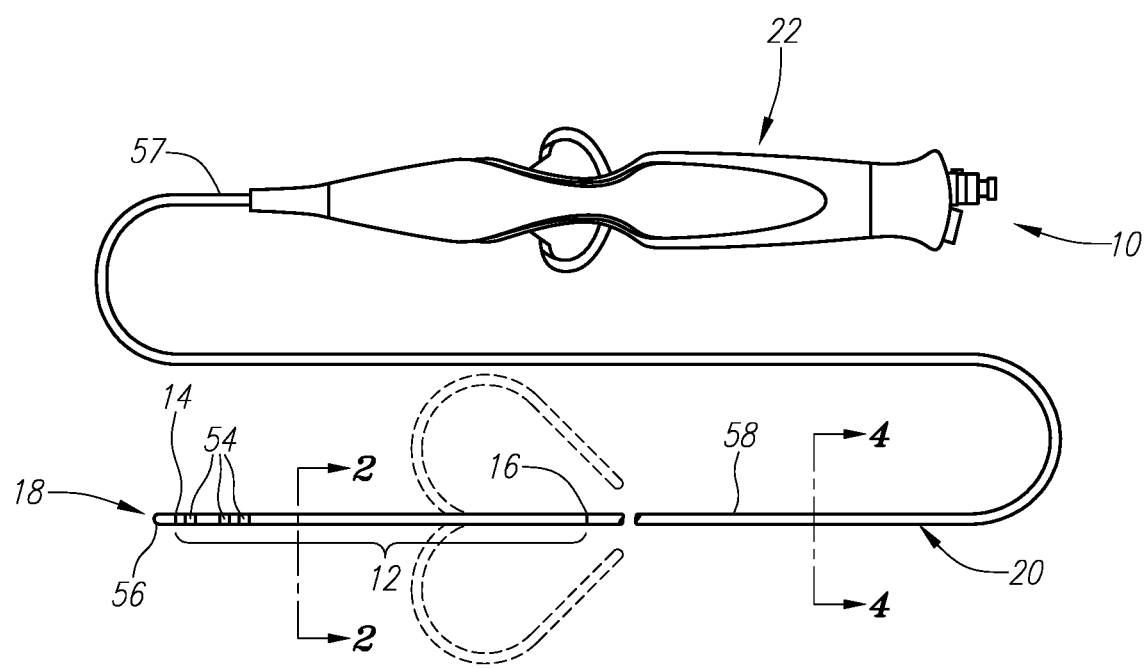
FIG. 1 is a schematic view of a catheter incorporating a deflectable catheter shaft section in accordance with an embodiment of the invention.

FIG. 1 generally illustrates a deflectable electrophysiology catheter 10 that comprises a deflectable catheter shaft section or distal deflectable section 12 in accordance with an embodiment of the disclosure. Deflectable catheter shaft section 12 comprises an elongated body having a distal end 14 and a proximal end 16. In its most general form, catheter 10 further comprises a tip assembly 18 located at the distal end 14 of the deflectable catheter shaft section 12, a proximal catheter shaft section 20 (including a proximal end 57 and a distal end 58) located proximal to the proximal end 16 of the deflectable catheter shaft section 12, and a handle assembly 22. Deflectable catheter shaft section 12 and proximal catheter shaft section 20 can be made of braided Pebax™ tube 60 (see FIGS. 2 and 4). Deflectable catheter shaft section 12 can also include one or more electrodes, such as ring electrodes 54 and tip electrode 56, for example. Catheter 10 may be used in any number of diagnostic and therapeutic applications, such as the recording of electrograms in the heart, the performance of a cardiac ablation procedure, and other similar applications/procedures.

Still referring to FIG. 1, deflectable catheter shaft section 12 is disposed between the tip assembly 18 and the proximal catheter shaft section 20. The length and diameter of the deflectable catheter shaft section 12 can vary according to the application. Generally, the length of the deflectable catheter shaft section 12 can range from about 2 inches (50.8 mm) to about 6 inches (152.4 mm) and the diameter of the deflectable catheter shaft section 12 can range from about 5 French to about 12 French. The diameter of the deflectable catheter shaft section 12 can be about 7 French in accordance with some embodiments of the disclosure. Although these particular dimensions are mentioned in particular, the dimensions of the deflectable catheter shaft section 12 can vary in accordance with various applications of the deflectable catheter shaft section 12. The deflectable catheter shaft section 12 can be configured for deflection independent of, or substantially independent of, the proximal catheter shaft section 20.

Figure 2:
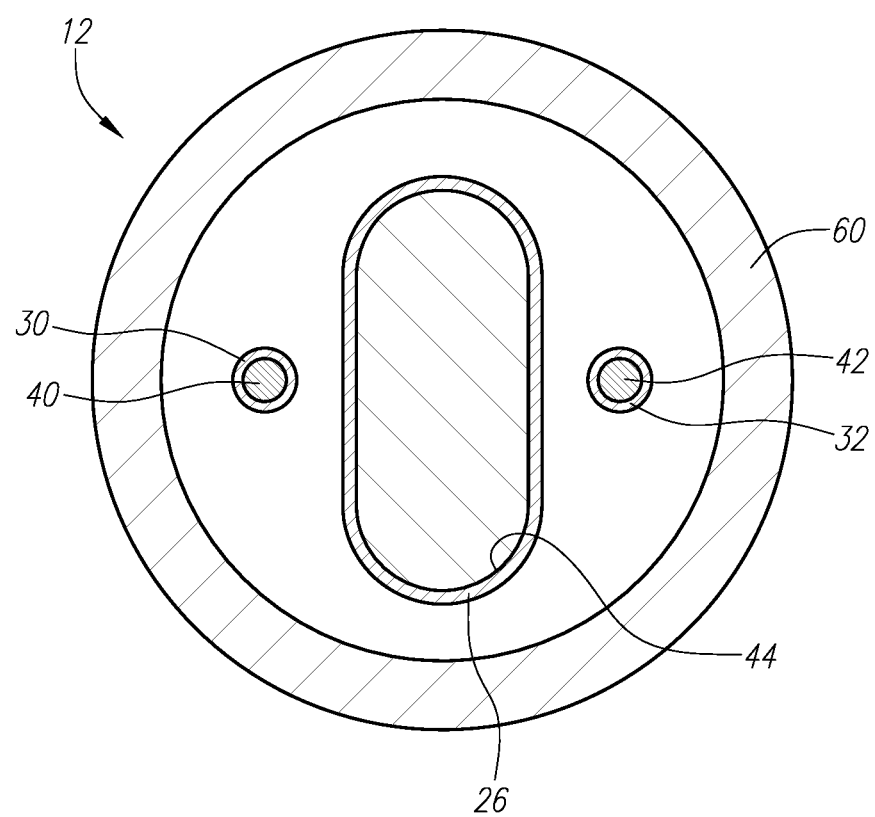
FIG. 2 is a schematic cross-sectional view of the deflectable catheter shaft section of FIG. 1 taken along line 2-2, with various components of the catheter omitted for clarity.

FIG. 2 illustrates a schematic cross-section of the deflectable catheter shaft section 12 taken along line 2-2, as shown in FIG. 1. In the illustrated embodiment, the deflectable catheter shaft section 12 comprises three substantially separate lumens formed by tubes 26, 30, and 32, each extending along the longitudinal axis of deflectable catheter shaft section 12. In another embodiment, deflectable catheter shaft section 12 may include fewer or more than three lumens. The lumens of tubes 26, 30, and 32 may extend along the entire length of deflectable catheter shaft section 12 or less than the entire length of deflectable catheter shaft section 12. Each lumen of tubes 26, 30, 32 may be formed to have a predetermined cross-sectional profile and shape. Each lumen of tubes 26, 30, 32 may be lined with liners (not shown) which may be attached to an inner surface of tubes 26, 30, or 32, such as the inner surface 44 of tube 26, for example. The liners may serve the purpose of providing a lubricious surface (e.g., to allow for the sliding of the pull wires) and insulating the components within the lumens of tubes 26, 30, 32. If provided, the liners may be constructed of a polymeric material, such as polytetraflouroethylene (PTFE) or any other suitable material.

The lumen of tube 26 may be configured to house wiring for electrodes or for other electrical components. The lumen of tube 26 may also be configured for use as an irrigation fluid passageway and the like. The lumens of tubes 30 and 32, which may be parallel to and located on opposite lateral sides of deflectable catheter shaft section 12, may be configured to house pull wires 40 and 42, respectively, to enable the deflectable catheter shaft section 12 to deflect in two or more directions. In particular, the handle assembly 22 may comprise at least one pull wire operatively connected to it to facilitate deflection of the deflectable catheter shaft section 12. Although the deflectable catheter shaft section 12 is described and illustrated as including two opposing pull wires 40, 42, it should be noted that the deflectable catheter shaft section 12 of catheter 10 is not limited to two opposing pull wires 40, 42. Rather, the deflectable catheter shaft section 12 of catheter 10 may include a single pull wire arrangement in other embodiments. The deflectable catheter shaft section 12 of catheter 10 may include more than two pull wires in other embodiments. The pull wires 40, 42 may be formed from a superelastic nickel-titanium (known as NiTi or Nitinol) wire, carbon fiber, para-aramid synthetic fiber generally available from DuPont under the brand name KEVLAR®, or other suitable material in accordance with various embodiments of the disclosure.

Figure 3:
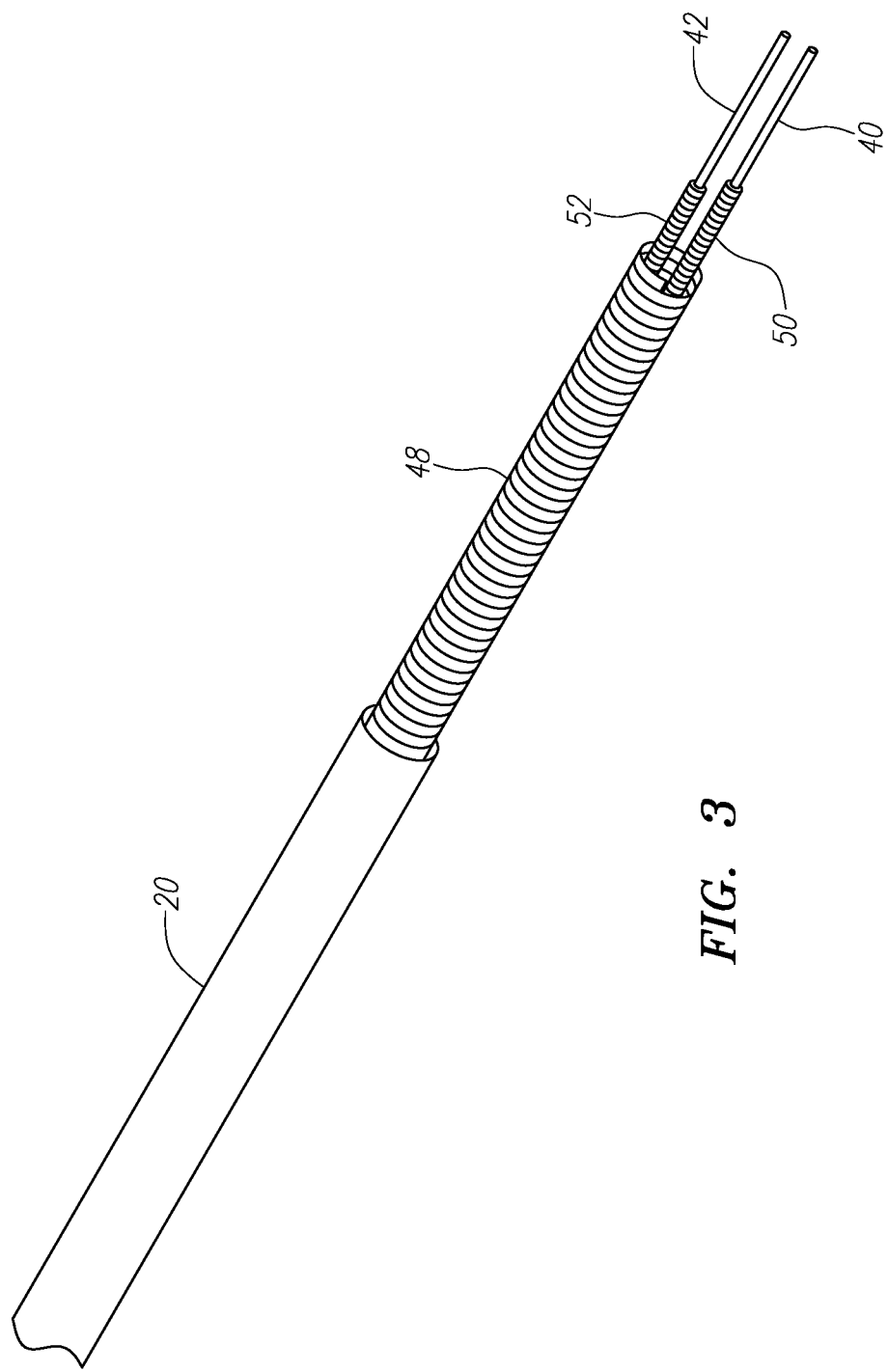
FIG. 3 is an isometric view of a proximal catheter shaft section, showing three compression resistance coils within the shaft.

Referring now to FIG. 3, the proximal catheter shaft section 20 of catheter 10 is shown comprising three distinct tightly-wound compression coils to provide compression resistance and deflection support during deflection of catheter 10. In other embodiments, fewer or more than three compression coils can be utilized. Body compression coil 48 is the largest of the three compression coils. Body compression coil 48, which may be made of wound stainless steel flat wire, can be strung through and thermally bonded within the proximal catheter shaft section 20. Moreover, body compression coil 48 can be anchored at the proximal end 57 (see FIG. 1) of the proximal catheter shaft section 20 and at the proximal end 16 of the deflectable catheter shaft section 12 via adhesive bonding, radiofrequency bonding, thermal bonding, or other mechanisms of attachment. Other internal catheter components, including pull wires 40 and 42, and tube 26 forming the electrical/fluid lumen (see FIGS. 2 and 4), can be strung through body compression coil 48.

Pull wire compression coils 50 and 52 are smaller in diameter than body compression coil 48, and are configured to surround pull wires 40 and 42, respectively. In an embodiment, pull wire compression coils 50 and 52 can be wound out of wound stainless steel flat wire, similar to body compression coil 48. Pull wires 40 and 42 can be strung through pull wire compression coils 50 and 52, respectively. Additionally, pull wire compression coils 50 and 52 can be adhesively bonded within the proximal end 57 of the proximal catheter shaft section 20 and thermally bonded within the proximal end 16 of the deflectable catheter shaft section 12 of the catheter 10. Moreover, pull wire compression coils 50 and 52 can be bonded within the proximal end 57 of the proximal catheter shaft section 20 and within the proximal end 16 of the deflectable catheter shaft section 12 via other mechanisms of attachment, such as radiofrequency bonding, for example. In an embodiment, pull wire compression coils 50 and 52 can be equal in length for symmetric deflection. In another embodiment, pull wire compression coils 50 and 52 can be unequal in length for asymmetric deflection.

The triple compression coil catheter embodiment illustrated in FIG. 3 has the primary benefit of maximizing resistance to compression of the proximal catheter shaft section 20 during deflection of catheter 10. This promotes resistance to snaking, or axial deformation, of the proximal catheter shaft section 20 during deflection. Moreover, resistance to compression in the proximal catheter shaft section 20 can maximize the curve angle that the deflectable catheter shaft section 12 can achieve. Additionally, the triple coil system promotes a more flexible proximal catheter shaft section 20 over the use of alternative methods. Finally, the triple coil system allows for a lower initial compression load on catheter 10, since each coil is progressively loaded as the axial load on the proximal catheter shaft section 20 increases. This lower initial compression load leads to a lower tensile load on the proximal catheter shaft section 20.

Figure 4:
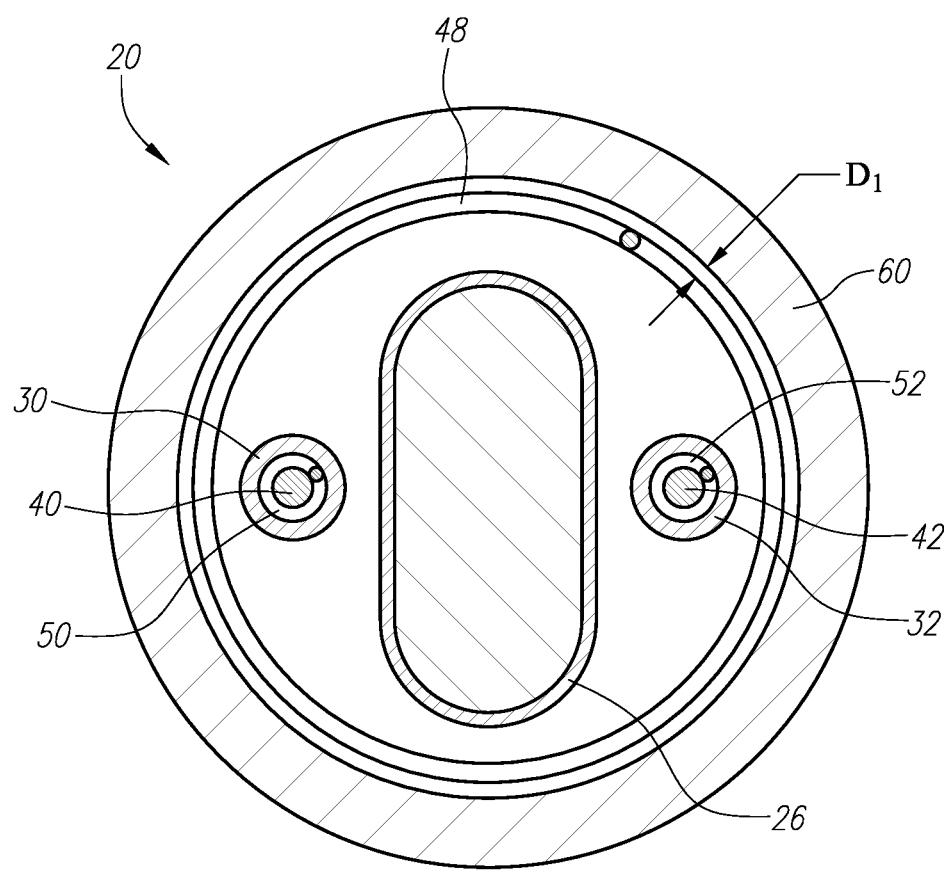
FIG. 4 is a schematic cross-sectional view of the proximal catheter shaft section of FIG. 1 taken along line 4-4, with various components of the catheter omitted for clarity.

FIG. 4 illustrates a schematic cross-section of the proximal catheter shaft section 20 taken along line 4-4, as shown in FIG. 1. Body compression coil 48 lies in between the Pebax™ tube 60 that forms at least the outer material the proximal catheter shaft section 20 and the internal contents of the proximal catheter shaft section 20. In an embodiment, there may be a gap $D_1$ between the outer circumference of the body compression coil 48 and the inner circumference of the Pebax™ tube 60 of about 0.0005-0.0010 inches. It has been found that such a gap can be beneficial for preventing or minimizing snaking of proximal catheter shaft section 20 and maximizing the inner diameter of the lumen of proximal catheter shaft section 20. FIG. 4 also illustrates pull wire compression coils 50 and 52 positioned within tubes 30 and 32 forming the pull-wire lumens.

Figure 5:
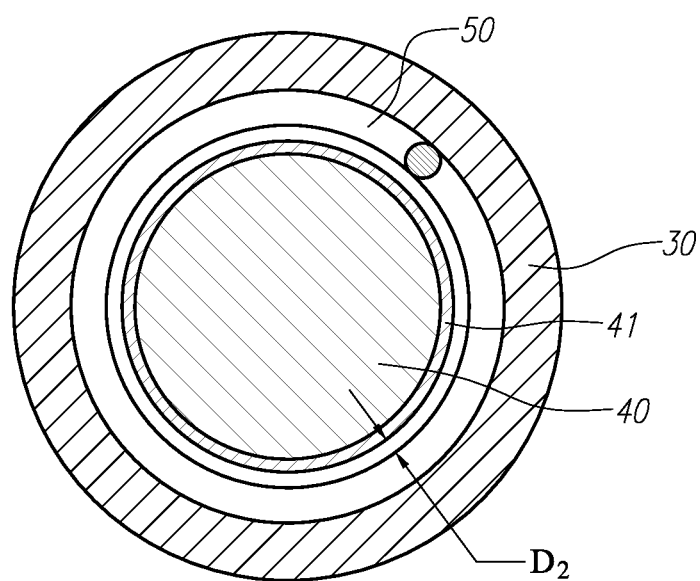
FIG. 5 is an enlarged, schematic cross-sectional view of a pull wire and its surrounding compression coil.

FIG. 5 is an enlarged, schematic cross-sectional view of pull wire 40 and its surrounding compression coil 50. In this embodiment, pull wire 40 includes a lubricous and durable coating 41, such as PTFE, for example. The coating 41 can be applied via a dip coat or spray coat process. Coating 41 allows for a reduction of the friction of coefficient between the pull wire 40 and the compression coil 50. This, in turn, lessens the amount of force required to deflect catheter 10.

In an embodiment, the gap size $D_2$ between the outer diameter of pull wire 40 (including coating 41) and the inner diameter of compression coil 50 can be about 10-30%, or about 20%, of the inner diameter of compression coil 50. It has been found that such a gap size $D_2$ provides optimal performance in terms of the force required for deflection and the torque response of catheter 10. The gap size $D_2$ allows enough space for the pull wire 40 to negotiate freely during deflection, and also enough space so that during articulation of the catheter 10, the internal components of the proximal catheter shaft section 20 do not bind up and cause whipping of the shaft.

In another embodiment, specific material and mechanical properties of pull wire 40 can be selected to improve the curve angle and curve shape of catheter 10. For example, minimization of the ultimate elongation and maximization of Young's Modulus for pull wire 40 can be achieved through maximization of the cold working of the wire, such that the material has the least amount of stretch and the greatest amount of tensile strength.

Although embodiments of a catheter shaft with compression coils have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments have been described above to various apparatuses, systems, and/or methods. Numerous specific details have been set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated above are non-limiting examples, and thus it can be appreciated that the specific structural and functional details disclosed above may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment.

Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" have been used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" have been used above with respect to the illustrated embodiments. However, surgical instruments may be used in many orientations and positions, and these terms are not intended to be limiting and absolute.

What is claimed is:

1. A steerable catheter comprising:
   a shaft comprising a proximal end, a distal end, and a central lumen;
   a distal deflectable section of the shaft, the distal deflectable section comprising a proximal end and a distal end;
   a body compression coil disposed within the shaft and extending through the central lumen from the proximal end of the shaft to the proximal end of the distal deflectable section;
   wherein a gap between an inner diameter of the shaft and an outer diameter of the body compression coil is about 0.0005-0.0010 inches;
   at least one internal compression coil extending through the body compression coil, the at least one internal compression coil extending from the proximal end of the shaft and terminating within the proximal end of the distal deflectable section; and
   a pull wire is disposed within the at least one internal compression coil, wherein a gap between an outer diameter of the pull wire and an inner diameter of the at least one internal compression coil is about 10%-30% of the inner diameter of the at least one internal compression coil.

2. The steerable catheter of claim 1, wherein the body compression coil is configured to maximize resistance to compression of the proximal end of the shaft during deflection and to minimize axial deformation of the proximal end of the shaft during deflection.

3. The steerable catheter of claim 1, wherein the body compression coil is configured to do at least one of the following: (a) maximize a curve angle of the distal deflectable section, (b) maximize flexibility of the proximal end of the shaft, and (c) lower an initial compression load on the catheter during deflection.

4. The steerable catheter of claim 1, wherein the body compression coil is configured to be progressively loaded as an axial load on the proximal end of the shaft increases.

5. The steerable catheter of claim 1, wherein the body compression coil comprises wound stainless steel flat wire.

6. The steerable catheter of claim 1, wherein the body compression coil is bonded within the proximal end of the shaft via at least one of the following mechanisms: radio frequency bonding, adhesive bonding, thermal bonding, or coupling.

7. The steerable catheter of claim 1, further comprising at least one of an electrical lumen or a fluid lumen extending through the body compression coil.

8. The steerable catheter of claim 1, wherein the gap is about 20% of the inner diameter of the at least one internal compression coil.

9. The steerable catheter of claim 1, wherein the pull wire includes a lubricious outer coating.

10. The steerable catheter of claim 9, wherein the outer diameter of the pull wire includes the lubricious outer coating.

11. A steerable catheter comprising:
    a shaft comprising a proximal end, a distal end, and a central lumen;
    a distal deflectable section of the shaft, the distal deflectable section comprising a proximal end and a distal end;
    a body compression coil disposed within the shaft and extending through the central lumen from the proximal end of the shaft to the proximal end of the distal deflectable section;
    a first internal compression coil; and
    a second internal compression coil, the first and second internal compression coils extending from the proximal end of the shaft and terminating within the proximal end of the distal deflectable section;
    wherein a gap between an inner diameter of the shaft and an outer diameter of the body compression coil is about 0.0005-0.0010 inches.

12. The steerable catheter of claim 11, wherein the body compression coil and the first and second internal compression coils are configured to maximize resistance to compression of the proximal end of the shaft during deflection and to minimize axial deformation of the proximal end of the shaft during deflection.

13. The steerable catheter of claim 11, wherein the body compression coil and the first and second internal compression coils are configured to do at least one of the following: (a) maximize a curve angle of the distal deflectable section, (b) maximize flexibility of the proximal end of the shaft, and (c) lower an initial compression load on the catheter during deflection.

14. The steerable catheter of claim 11, wherein the body compression coil and the first and second internal compression coils are each configured to be progressively loaded as an axial load on the proximal end of the shaft increases.

15. The steerable catheter of claim 11, wherein the body compression coil and at least one of the first and second internal compression coils comprise wound stainless steel flat wire.

16. The steerable catheter of claim 11, wherein the body compression coil is bonded within the proximal end of the shaft via at least one of the following mechanisms: radio frequency bonding, adhesive bonding, thermal bonding, or coupling.

17. The steerable catheter of claim 11, wherein at least one of the first and second internal compression coils is bonded proximally within the proximal end of the shaft and distally within the proximal end of the distal deflectable section; and wherein bonding occurs via at least one of the following mechanisms: radio frequency bonding, adhesive bonding, thermal bonding, or coupling.

18. The steerable catheter of claim 11, further comprising a pull wire disposed within at least one of the first and second internal compression coils.

19. The steerable catheter of claim 18, wherein a gap between an outer diameter of the pull wire and an inner diameter of at least one of the first and second internal compression coils is about 10%-30% of the inner diameter of the at least one of the first and second internal compression coils.

20. The steerable catheter of claim 19, wherein the gap is about 20% of the inner diameter of the at least one of the first and second internal compression coils.

\* \* \* \* \*